US012558184B2

(12) United States Patent
Trotter

(10) Patent No.: US 12,558,184 B2
(45) Date of Patent: Feb. 24, 2026

(54) SYSTEM AND METHOD FOR A NAVIGATED PROCEDURE

(71) Applicant: Medtronic Navigation, Inc., Louisville, CO (US)

(72) Inventor: Eric Trotter, Denver, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 388 days.

(21) Appl. No.: 17/910,663

(22) PCT Filed: Apr. 28, 2021

(86) PCT No.: PCT/US2021/029596
§ 371 (c)(1),
(2) Date: Sep. 9, 2022

(87) PCT Pub. No.: WO2021/222379
PCT Pub. Date: Nov. 4, 2021

(65) Prior Publication Data
US 2023/0149112 A1     May 18, 2023

Related U.S. Application Data

(60) Provisional application No. 63/017,106, filed on Apr. 29, 2020.

(51) Int. Cl.
A61B 90/11          (2016.01)
A61B 17/34          (2006.01)
(Continued)

(52) U.S. Cl.
CPC .......... A61B 90/11 (2016.02); A61B 17/3403 (2013.01); A61B 34/20 (2016.02);
(Continued)

(58) Field of Classification Search
CPC ......... A61B 90/11; A61B 34/20; A61B 34/30; A61B 17/3403; A61B 2034/2051;
(Continued)

(56) References Cited

U.S. PATENT DOCUMENTS 6,283,977 B1 *  9/2001  Ericsson ................ A61B 90/10
                                                            606/130
7,697,972 B2    4/2010  Verard et al.
(Continued)

FOREIGN PATENT DOCUMENTS

EP          3586784 A2        1/2020
WO    WO-2019008127 A1        1/2019
(Continued)

OTHER PUBLICATIONS

International Search Report and Written Opinion regarding International Application No. PCT/US2021/029596, dated Aug. 11, 2021. ISA/EP.
(Continued)

*Primary Examiner* — Mohamed G Gabr
*Assistant Examiner* — Khoa Tan Le
(74) *Attorney, Agent, or Firm* — Mueting Raasch Group

(57)          ABSTRACT

Disclosed is a guide or alignment system. The system may be used to at least assist in a procedure. The system may assist in aligning objects and/or determining physical boundaries for a selected portion of the procedure.

20 Claims, 6 Drawing Sheets

(51) Int. Cl.
| | |
|---|---|
| *A61B 34/20* | (2016.01) |
| *A61B 34/30* | (2016.01) |
| *A61B 90/00* | (2016.01) |

(52) U.S. Cl.
CPC ...... *A61B 34/30* (2016.02); *A61B 2017/3407* (2013.01); *A61B 2034/2051* (2016.02); *A61B 2034/2055* (2016.02); *A61B 2090/374* (2016.02)

(58) Field of Classification Search
CPC ...... A61B 2034/2055; A61B 2090/374; A61B 2017/3407
See application file for complete search history.

(56) References Cited

U.S. PATENT DOCUMENTS

| | | | |
|---|---|---|---|
| 8,301,226 | B2 | 10/2012 | Csavoy et al. |
| RE44,305 | E | 6/2013 | Foley et al. |
| 8,644,907 | B2 | 2/2014 | Hartmann et al. |
| 8,842,893 | B2 | 9/2014 | Teichman et al. |
| 8,886,331 | B2 | 11/2014 | Labadie et al. |
| 9,492,121 | B2 | 11/2016 | Andrews et al. |
| 10,092,367 | B2 * | 10/2018 | Andrews ................... A61F 5/37 |
| 2004/0199072 | A1 | 10/2004 | Sprouse et al. |
| 2016/0249990 | A1 | 9/2016 | Glozman et al. |
| 2016/0354175 | A1 * | 12/2016 | Andrews ............... A61B 5/015 |
| 2016/0367331 | A1 | 12/2016 | Nelson et al. |

FOREIGN PATENT DOCUMENTS

| | | | | |
|---|---|---|---|---|
| WO | WO-2020020749 | A1 * | 1/2020 | ............ A61B 34/20 |
| WO | 2021222379 | A1 | 11/2021 | |

OTHER PUBLICATIONS

International Preliminary Report on Patentability corresponding to PCT/US2021/029596, dated Oct. 27, 2022, with Written Opinion of the International Searching Authority EPO/ISA.

\* cited by examiner

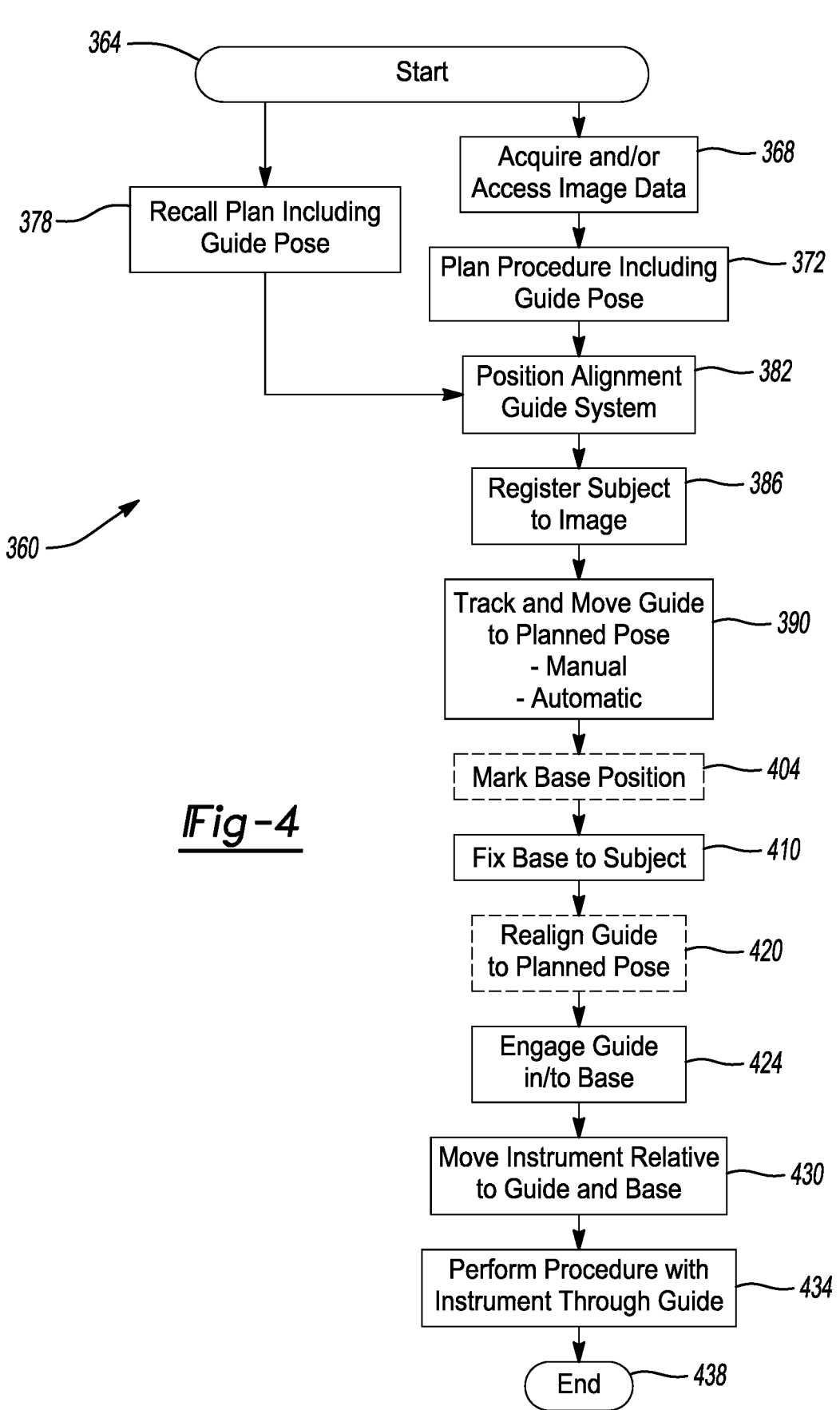
_Fig-4_

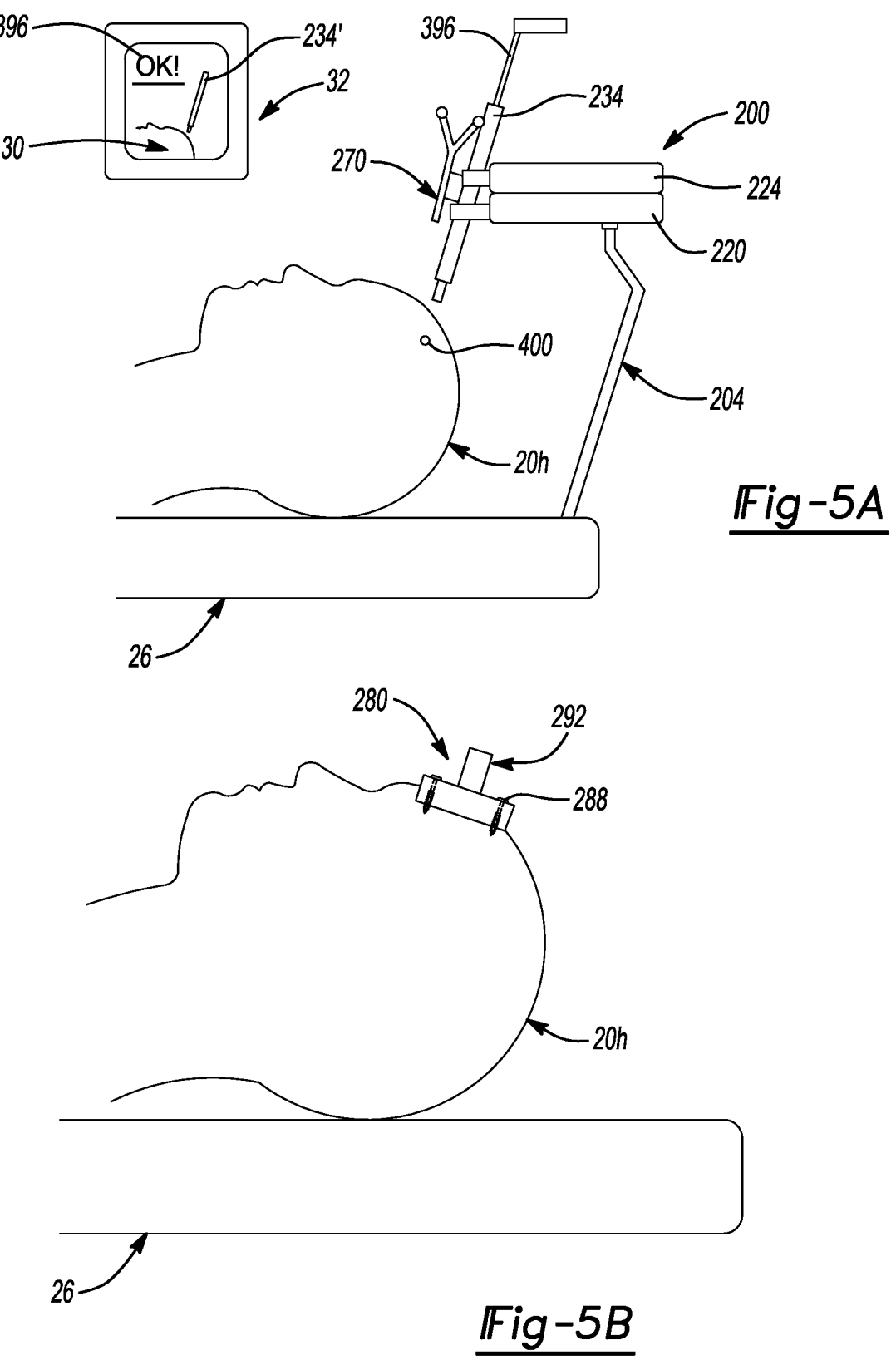
_Fig-5A_
_Fig-5B_

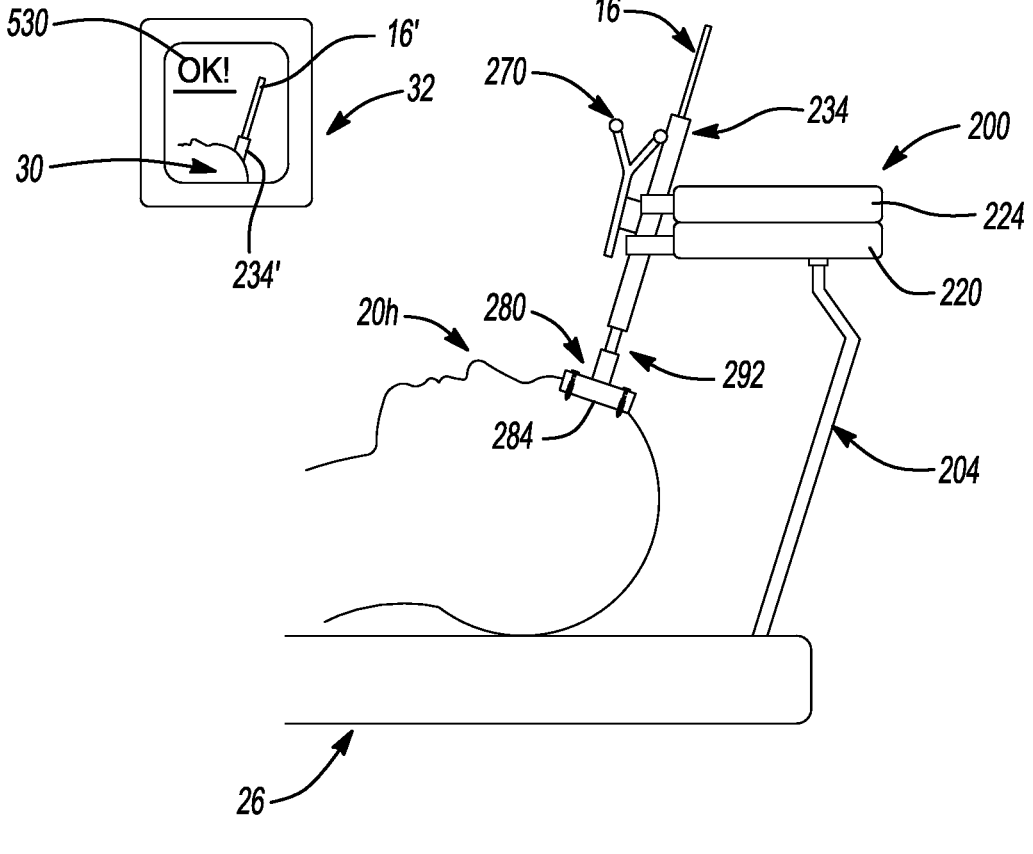
<u>*Fig-5C*</u>

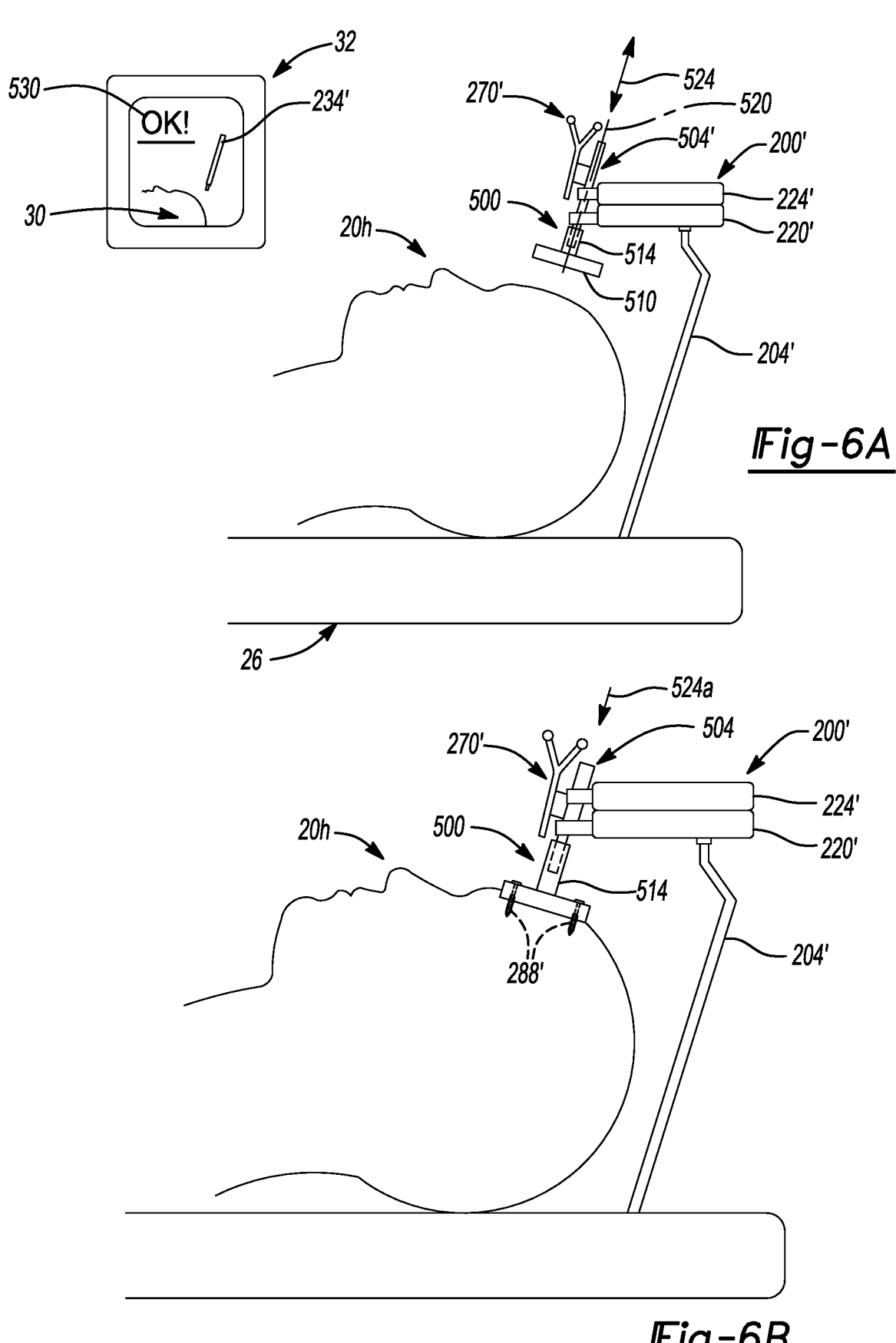
_Fig-6A_
_Fig-6B_

SYSTEM AND METHOD FOR A NAVIGATED PROCEDURE

CROSS REFERENCE TO RELATED APPLICATIONS

This application is a U.S. National Phase Application under 35 U.S.C. 371 of International Application No. PCT/US2021/029596, filed on Apr. 28, 2021, which claims priority to U.S. Patent Application No. 63/017,106, filed on Apr. 29, 2020. The entire disclosures of the above applications are expressly incorporated by reference herein.

FIELD

The subject disclosure relates generally to a system and method for determining and/or selecting a position, including location and orientation, of a member in space and/or relative to a subject.

BACKGROUND

This section provides background information related to the present disclosure which is not necessarily prior art.

In a navigation system for various procedures, such as surgical procedures, assembling procedures, and the like, an instrument or object may be tracked. The instrument may be tracked by one or more tracking systems of various operation modes, such as by measuring an effect of a magnetic field on a sensor coil and/or determining a location with optical sensors. The sensor coil may include a conductive material that is placed within a magnetic field where a current is induced in the sensor coil. The measured induced current may be used to identify or determine a position of the instrument or object.

The electro-magnetic field may be generated with a plurality of coils, such as three orthogonally placed coils. Various transmitter or field generation systems include the AxiEM™ electro-magnetic navigation system sold by Medtronic Navigation, Inc., having a place of business in Louisville, Colorado. The AxiEM™ electro-magnetic navigation system may include a plurality of coils that are used to generate an electro-magnetic field that is sensed by a tracking device, which may be the sensor coil, to allow a navigation system, such as a StealthStation® surgical navigation system, to be used to track and/or illustrate a tracked position of an instrument.

The tracking system may also, or alternatively, include an optical tracking system. Optical tracking systems include those such as the StealthStation® S7® tracking system. The optical tracking system includes a set of cameras with a field of vision to triangulate a position of the instrument.

SUMMARY

This section provides a general summary of the disclosure and is not a comprehensive disclosure of its full scope or all of its features.

A system for performing and/or preparing for a procedure is disclosed. The procedure may be performed on a living subject such as an animal, human, or other selected patient. The procedure may include any appropriate type of procedure, such as one being performed on an inanimate object (e.g. an enclosed structure, airframe, chassis, etc.). Nevertheless, the procedure may be performed using a navigation system where a tracking system is able to track a selected one or more items.

A navigation system may be used to navigate an instrument relative to a subject for performing a procedure. In various embodiments, the procedure may include a procedure on a spine such as a spinal fusion where two or more vertebrae are connected together with a selected implant system or assembly. The procedure may also be to obtain or gain access to a volume, such a cranial volume. In various embodiments, for example, and implant may be placed in a brain of subject.

The disclosed system includes an alignment guide that may be positioned relative to the subject. The alignment guide may include a member that may be fixed to the subject. Further the alignment guide may be moved with a selected system, such as a mechanical or robotic system relative to the subject. Appropriate robotic systems may include the Stealth Autoguide® cranial robotic guidance platform sold by Medtronic, Inc., having a place of business in Louisville, CO.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 4 is a flow chart of a procedure using an alignment system;

Figure 1:
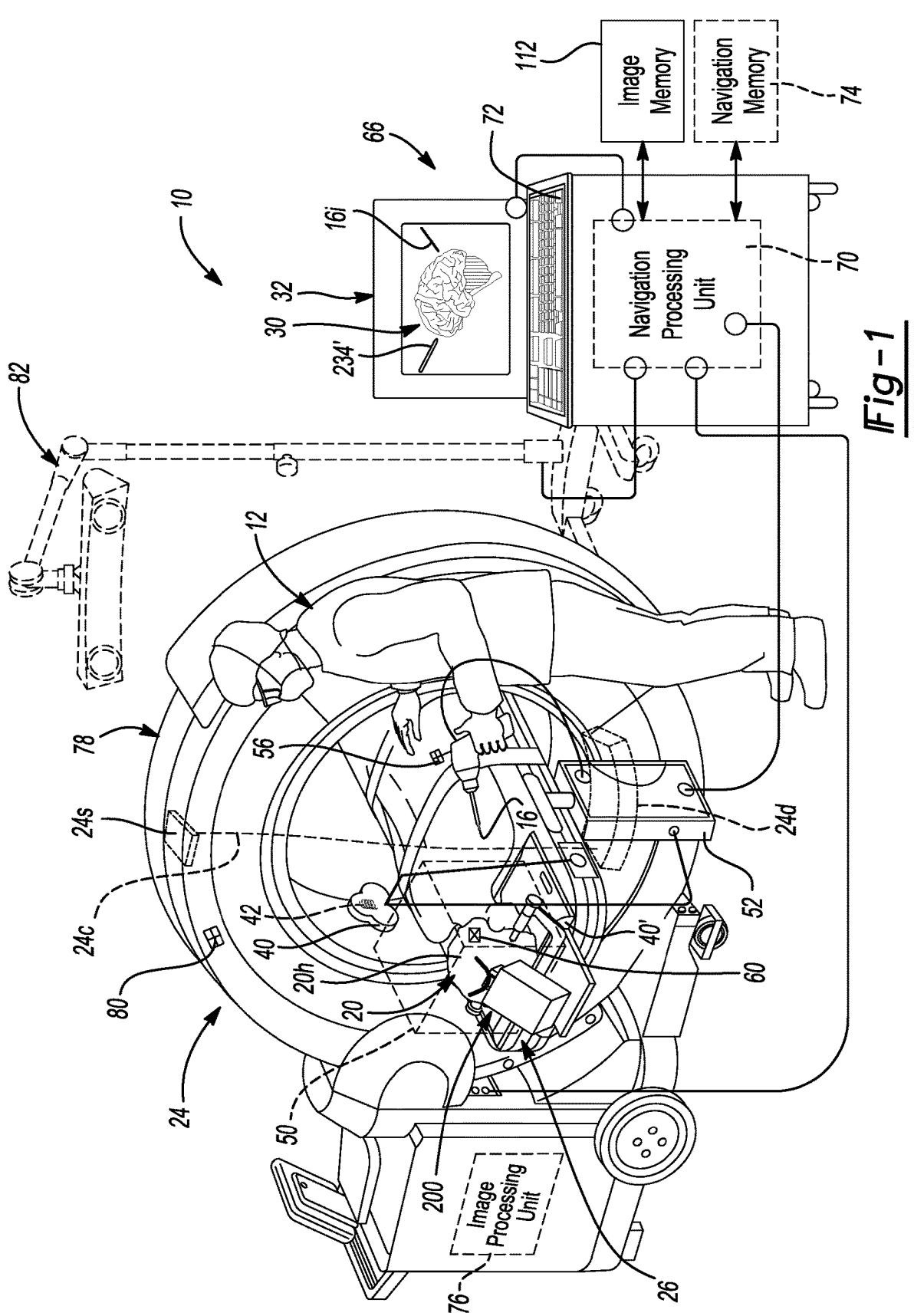
FIG. 1 is an environmental view of a navigation system.

FIGS. 5A, 5B, and 5C show in series the use of the alignment system, according to various embodiments; and FIGS. 6A and 6B illustrate use of an alignment system, according to various embodiments.

Corresponding reference numerals indicate corresponding parts throughout the several views of the drawings.

DETAILED DESCRIPTION

Example embodiments will now be described more fully with reference to the accompanying drawings.

With initial reference to FIG. 1, a navigation system 10 is illustrated. The navigation system 10 may be used for various purposes or procedures by one or more users, such as a user 12. The navigation system 10 may be used to determine or navigate a position (also referred to as a pose) of an instrument 16 in a volume. The position may include at least six degrees of freedom, including three dimensional X, Y, Z location and one or more degrees of orientation. Orientation may include one or more degree of freedom, such as three degrees of freedom including yaw, pitch, and roll. It is understood, however, that any appropriate degree of freedom position information, such as less than six-degree of freedom position information, may be determined and/or presented to the user 12.

Navigating the position of the instrument 16 may be done with a first or instrument tracking device 56 and may assist the user 12 in knowing and/or understanding a position of the instrument 16, even if the instrument 16 is not directly viewable by the user 12, relative to a selected frame of reference, such as an image frame of reference and, therefore, relative to a subject 20. Various procedures may block the view of the user 12, such as performing a repair or assembling an inanimate system, such as a robotic system, assembling portions of an airframe or an automobile, or the like. Various other procedures may include a surgical procedure, such as performing a spinal procedure, neurological procedure, positioning a deep brain simulation probe, or other surgical procedures on a living subject. In various embodiments, for example, the subject 20 may be a human subject 20 and the procedure may be performed on the human subject 20. It is understood, however, that the instrument 16 may be tracked and/or navigated relative to any subject for any appropriate procedure. Tracking or navigating an instrument for a procedure, such as a surgical procedure, on a human or living subject is merely exemplary.

In various embodiments, the surgical navigation system 10, as discussed further herein, may incorporate various portions or systems, such as those disclosed in U.S. Pat. Nos. RE44,305; 7,697,972; 8,644,907; and 8,842,893; and U.S. Pat. App. Pub. No. 2004/0199072, all incorporated herein by reference. Various components that may be used with or as a component of the surgical navigation system 10 may include an imaging system 24 that is operable to image the subject 20, such as an O-arm® imaging system, magnetic resonance imaging (MRI) system, computed tomography system, etc. A subject support 26 may be used to support or hold the subject 20 during imaging and/or during a procedure. The same or different supports may be used for different portions of a procedure.

In various embodiments, the imaging system 24 may include a source 24s. The source may emit and/or generate X-rays. The X-rays may form a cone 24c, such as in a cone beam, that impinge on the subject 20. Some of the X-rays pass though and some are attenuated by the subject 20. The imaging system 24 may further include a detector 24d to detect the X-rays that are not completely attenuated, or blocked, by the subject 20. Thus, the image data may include X-ray image data. Further, the image data may be two-dimensional (2D) image data.

Image data may be acquired, such as with one or more of the imaging systems discussed above, during a surgical procedure or acquired prior to a surgical procedure for displaying an image 30 on a display device 32. In various embodiments, the acquired image data may also be used to form or reconstruct selected types of image data, such as three-dimensional volumes, even if the image data is 2D image data. The instrument 16 may be tracked in a trackable volume or a navigational volume (also referred to as subject space defined relative to the subject 20) by one or more tracking systems. Tracking systems may include one or more tracking systems that operate in an identical manner or more and/or different manner or mode. For example, the tracking system may include an electro-magnetic (EM) localizer 40, as illustrated in FIG. 1. In various embodiments, it is understood by one skilled in the art, that other appropriate tracking systems may be used including optical tracking system that may include an optional tracking system localizer 82, radar, ultrasonic, etc. The discussion herein of the EM localizer 40 and tracking system is merely exemplary of tracking systems operable with the navigation system 10.

The position of the instrument 16 may be tracked in the tracking volume relative to the subject 20 and then illustrated as a graphical representation, also referred to as an icon, 16i with the display device 32. In various embodiments, the icon 16i may be superimposed on the image 30 and/or adjacent to the image 30. As discussed herein, the navigation system 10 may incorporate the display device 30 and operate to render the image 30 from selected image data, display the image 30, determine the position of the instrument 16, determine the position of the icon 16i, etc.

The EM localizer 40 (and or alternative localizer 40') is operable to generate electro-magnetic fields with a transmitting coil array (TCA) 42 which is incorporated into the localizer 40. The TCA 42 may include one or more coil groupings or arrays. In various embodiments, more than one group is included and each of the groupings may include three coils, also referred to as trios or triplets. The coils may be powered to generate or form an electro-magnetic field by driving current through the coils of the coil groupings. As the current is driven through the coils, the electro-magnetic fields generated will extend away from the coils 42 and form a navigation domain or volume 50, such as encompassing all or a portion of a head 20h, spinal vertebrae 20v, or other appropriate portion. The coils may be powered through a TCA controller and/or power supply 52. It is understood, however, that more than one of the EM localizers 40 may be provided and each may be placed at different and selected locations.

The navigation domain or volume 50 generally defines a navigation space or patient space. As is generally understood in the art, the instrument 16, such as a drill, lead, guide tube, guide member, lead, etc., may be tracked in the navigation space that is defined by a navigation domain relative to a patient or subject 20 with the instrument tracking device 56. For example, the instrument 16 may be freely moveable, such as by the user 12, relative to a dynamic reference frame (DRF) or patient reference frame tracker 60 that is fixed relative to the subject 20. Both the tracking devices 56, 60 may include tracking portions that are tracking with appropriate tracking systems, such as sensing coils (e.g. conductive material formed or placed in a coil) that senses and are used to measure a magnetic field strength, optical reflectors and/or emitters, ultrasonic emitters, etc. Due to the tracking device 56 connected or associated with the instrument 16, relative to the DRF 60, the navigation system 10 may be used to determine the position of the instrument 16 relative to the DRF 60.

The navigation of a moveable portion relative to the subject 20 (which may include determining and illustrating a position of a tracked portion) may be made due to a registration of the subject space relative to an image space. The navigation volume or patient space may be registered to an image space defined by the image 30 of the subject 20 and the icon 16i representing the instrument 16 may be illustrated at a navigated (e.g. determined) and tracked position with the display device 32, such as superimposed on the image 30. Registration of the patient space to the image space and determining a position of a tracking device, such as with the tracking device 56, relative to a DRF, such as the DRF 60, may be performed as generally known in the art, including as disclosed in U.S. Pat. Nos. RE44,305; 7,697, 972; 8,644,907; and 8,842,893; and U.S. Pat. App. Pub. No. 2004/0199072, all incorporated herein by reference. Generally, registration includes a translation between the subject space and the image space. This may be done by identifying points in the subject space (i.e. fiducial portions) and identifying the same points in the image (i.e. image fiducials). A translation map of the image space to the subject space may then be made, such as by the navigation system 10.

The navigation system 10 may further include a navigation processor system 66. The navigation processor system 66 may include the display device 32, the TCA 40, the TCA controller 52, and other portions and/or connections thereto. For example, a wire connection may be provided between the TCA controller 52 and a navigation processing unit or module 70. Further, the navigation processor system 66 may have one or more user control inputs, such as a keyboard 72, and/or have additional inputs such as from communication with one or more memory systems 74, either integrated or via a communication system. The navigation processor system 66 may, according to various embodiments include those disclosed in U.S. Pat. Nos. RE44,305; 7,697,972; 8,644,907; and 8,842,893; and U.S. Pat. App. Pub. No. 2004/0199072, all incorporated herein by reference, or may also include the commercially available StealthStation® or Fusion™ surgical navigation systems sold by Medtronic Navigation, Inc. having a place of business in Louisville, CO.

Tracking information, including information regarding the magnetic fields sensed with the tracking devices 56, 60, may be delivered via a communication system, such as the TCA controller, which also may be a tracking device controller 52, to the navigation processor system 66 including the navigation processor 70. Thus, the tracked position of the instrument 16 may be illustrated as the icon 16i relative to the image 30. Various other memory and processing systems may also be provided with and/or in communication with the processor system 66, including the memory system 72 that is in communication with the navigation processor 70 and/or an imaging processing unit 76 including an imaging or image memory 112. The image memory 112 may store or be used for recall of images or image data acquired of the subject 20, such as by the imaging system 24 or other appropriate imaging system.

The image processing unit 76 may be incorporated into the imaging system 24, such as the O-arm® imaging system, as discussed above. The imaging system 24 may, therefore, include various portions such as a source and an x-ray detector that are moveable within a gantry 78. The imaging system 24 may also be tracked with an imaging tracking device 80. It is understood, however, that the imaging system 24 need not be present while tracking the tracking devices, including the instrument tracking device 56. Also, the imaging system 24 may be any appropriate imaging system including a MRI, CT, etc.

In various embodiments, the tracking system may include the optical localizer 82. The optical localizer 82 may include one or more cameras that view or have a field of view that defines or encompasses the navigation volume 50. The optical localizer 82 may receive light (e.g. infrared or ultraviolet) input to determine a position or track the tracking device, such as the instrument tracking device 56. It is understood that the optical localizer 82 may be used in conjunction with and/or alternatively to the EM localizer 40 for tracking the instrument 16.

Information from all of the tracking devices may be communicated to the navigation processor 70 for determining a position of the tracked portions relative to each other and/or for localizing the instrument 16 relative to the image 30. The imaging system 24 may be used to acquire image data to generate or produce the image 30 of the subject 20. It is understood, however, that other appropriate imaging systems may also be used. The TCA controller 52 may be used to operate and power the EM localizer 40, as discussed above.

The image 30 that is displayed with the display device 32 may be based upon image data that is acquired of the subject 20 in various manners. For example, the imaging system 24 may be used to acquire image data that is used to generate the image 30. It is understood, however, that other appropriate imaging systems may be used to generate the image 30 using image data acquired with the selected imaging system. Imaging systems may include magnetic resonance imagers, computed tomography imagers, and other appropriate imaging systems. Further the image data acquired may be two dimensional or three dimensional data and may have a time varying component, such as imaging the patient during a heart rhythm and/or breathing cycle.

In various embodiments, the image data is a 2D image data that is generated with a cone beam. The cone beam that is used to generate the 2D image data may be part of an imaging system, such as the O-arm® imaging system. The 2D image data may then be used to reconstruct a 3D image or model of the imaged subject, such as the patient 20. The reconstructed 3D image and/or an image based on the 2D image data may be displayed. Thus, it is understood by one skilled in the art that the image 30 may be generated using the selected image data.

Further, the icon 16i, determined as a tracked position of the instrument 16, may be displayed on the display device 32 relative to the image 30. In addition, the image 30 may be segmented, for various purposes, including those discussed further herein. Segmentation of the image 30 may be used determine and/or delineate objects or portions in the image. In various embodiments, the image may include a segmented brain for assisting or performing a selected procedure relative to the brain such as placement of a deep brain stimulation (DBS) lead.

As discussed above, the navigation system 10 may be used to navigate, such as by tracking devices, various portions, such as with the localizer 40. The various portions may be navigated for purposes of identifying positions of the tracked portions relative to the subject 20, registration of image data to the subject 20, and other appropriate purposes. In various embodiments, a guide assembly or system 200 may be used relative to the subject 20 for a selected portion of the procedure.

Figures 2, 3, 3A:
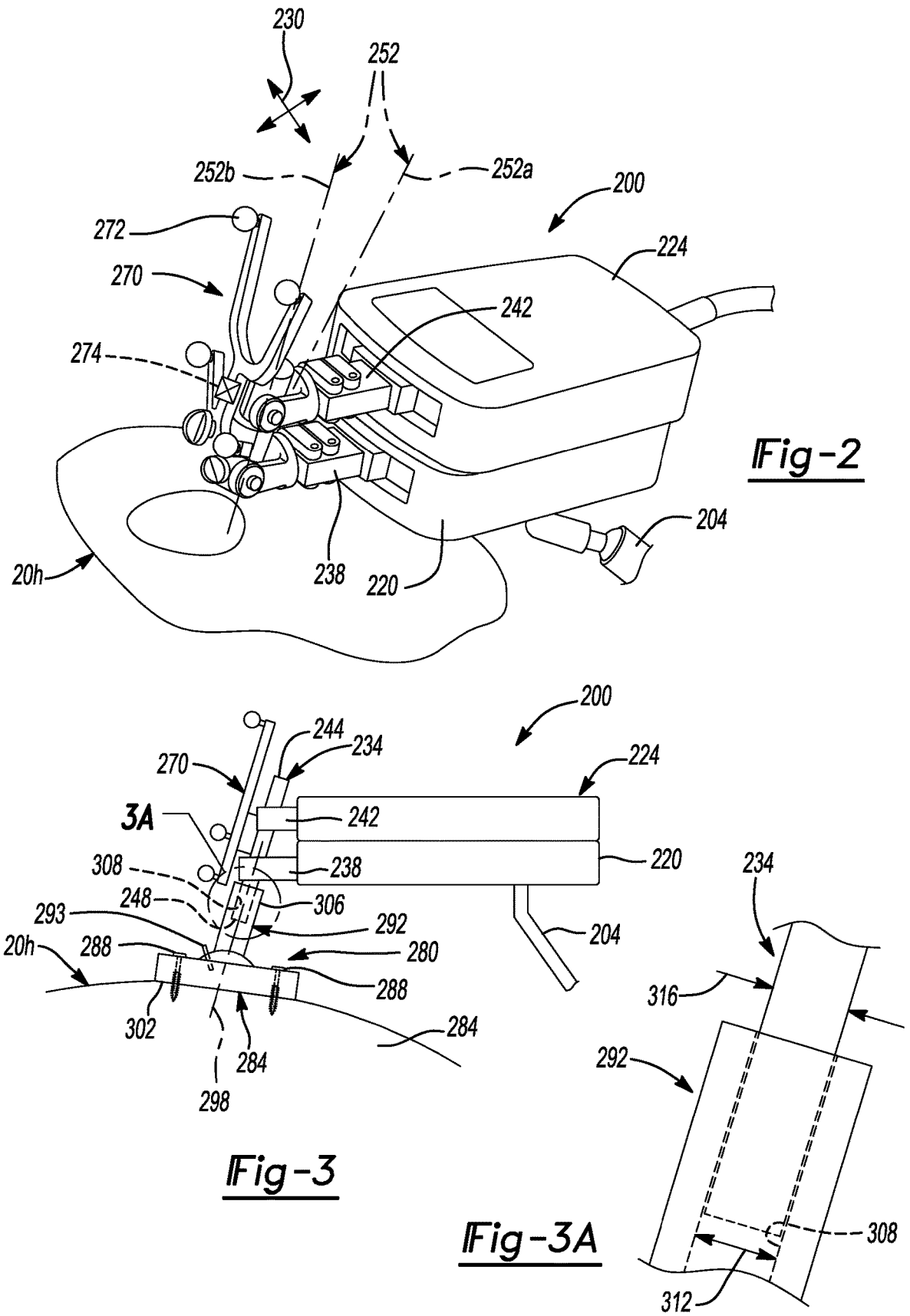
FIG. 2 is an adjustable guide system of the alignment system, according to various embodiments.
FIG. 3 is an assembled view of an alignment system including a guide member and an adjustable base, according to various embodiments.
FIG. 3A is a detail view of the guide system and an adjustable base.

With continuing reference to FIG. 1 and additional reference to FIG. 2, the alignment system 200 may be positioned relative to the subject 20, such as with a mounting system or construct 204 that may be fixed to the bed or support 26. The guide system 200 may be positioned and/or fixed relative to the subject 20. The support structure 204 may be a rigid structure and/or a movable and fixable support structure, such as the Vertek® flexible support arm system sold by Medtronic Navigation, Inc., having a place of business in Louisville, Colorado. The flexible or moveable support 204 may also be fixed relative to the subject 20 in a selected location after being moved to the selected location. Thus, the guide system 200 may be fixed relative to the subject 20 and/or moved relative to the subject 20.

At an appropriate position, the guide system 200 may have a first or fixed portion 220 that may be connected directly to the support 204. The guide system 200 may further include a second or movable portion 224 that may move relative to the base or first portion 220. The movable portion 224 may move or translate in a plane in any appropriate position or translation amount relative to the fixed portion 220. Accordingly, the movable portion 224 may generally move in a planar or axis system 230 relative to the base portion 220. The guide system 200 may include the Stealth Autoguide® cranial robotic guidance platform sold by Medtronic, Inc., having a place of business in Louisville, CO. Thus, the guide system may be controlled by the user 12 and/or other appropriate portion to move relative to the subject 20.

The guide system 200 may further include a guide member. The guide member may be a guide tube 234 that may have a bore or through bore, as discussed herein. The guide tube 234 may be held relative to the base portion 220 with a first holding or fixation portion 238. The guide tube 234 may also be fixed or held relative to the second portion 224 with a second holding or fixation portion 242. The respective holding portions 238, 242 may fixedly hold two portions of the guide tube 234, such as near a first end or entry portion 244 of the guide tube and near a second end 248. The fixation portions 238, 242 may have a fixed length relative to the respective members 220, 224 and the tube 234. Accordingly, the respective ends of the tube 244, 248 are fixed at respective distances from the respective members 220, 224.

The fixation members 238, 242, however, may include joints to allow movement of the second member 224 relative to the first member 220 and thereby also moving the tube 234. As illustrated in FIG. 2, the tube 234 may extend along an axis 252. The guide tube 234 may be at a first position 252a. The second member 224 may translate relative to the first member 220, such as any of the directions 230, and this may cause the tube 234 and the respective axis 252 to move from the first position 252a to a second position 252b. Thus, movement between the second member 224 and the first member 220 may move the tube 234 to move the long axis 252 relative to the subject 20. Therefore, the position or trajectory of the alignment of the tube 234 may be adjusted relative to the subject 20.

The position of the tube 234 may be determined. The position of the tube 234 may also be illustrated on the display device 32, as discussed above, due to the determined position. In various embodiments, affixed to and/or associated with the tube 234 may be a tube or alignment guide tracking device 270. The tracking device may be tracked to determine the position of the tube 234.

The tracking device 270 may be any appropriate tracking device such as an EM tracking device and/or an optical tracking device. In various embodiments, the tracking device 270 may include optical trackable portions, such as reflective spheres 272 and/or may include one or more coils operable with the EM localizer 40. As discussed above, the tracking device 270 may be tracked with the navigation system 10 to navigate or determine a position of the guide 234 relative to the subject 20. Again, the tracking device 270 may be tracked and the position of the tube 234, associated with the guide tracking device 270, may be illustrated with the display device 32, such as with an icon 234' relative to the image 30. The alignment system 200, therefore, may move the long axis 252 of the tube within a selected cone relative to the subject 20. The apex of the cone may be moved by moving the support 204 and/or the subject 20.

In various embodiments, the position of the guide 234 may be tracked or determined with other tracking portions. For example, the alignment system may include internal or selected sensors, such as encoders, to determine movement and position of the guide 234. Thus, the tracking device 270 may not be required to track the guide 234. The determined movement or position of the alignment system 200 may be used to navigate the guide 234.

With continuing reference to FIG. 2, and additional reference to FIG. 3, the alignment system 200 may include the movable portion or adjustable portion including the first and second members 220, 224 and the guide 234 that may be moved thereby, as discussed above. In addition to the movable portions, as discussed above, the alignment system 200 may include a base assembly 280. The base assembly may include a selected number of portions, such as a base portion or member 284 that may be fixed to the skull 20h of the subject 20. In various embodiments, the base portion 284 may be fixed to the skull 20h or selected fixation members, such as bone screws 288. An appropriate number of the screws 288, or other appropriate fixation members, may be used to fix the base 284 to the skull 20h.

Extending or associated with the base portion 284 may be an adjustable member 292. The adjustable member 292 may extend along a long axis 298 that may be fixed and/or selectively fixed relative to the base portion 284. Thus, the adjustable member 292 may be positioned relative to a base surface 302 of the base portion 284. A fixation system or member may selectively fix the adjustable member 292 relative to the base portion 284. For example, a locking member or set screw 293 may engage the adjustable member 292 relative to the base portion 284. Thus, the locking member 293 may be selectable between and engaged or locked position and an unengaged or unlocked position. In the unlocked position, the adjustable member 292 may be moved relative to the base portion 284. In the locked position, the adjustable member 292 may be fixed relative to the base portion 284.

The adjustable member 292 may include an external surface or wall 306 and an internal surface 308. The alignment guide 234 may be positioned within the adjustable member 292 and may selectively engage the internal wall 308. Accordingly, the guide tube 234 may be aligned with the adjustment system 200 and may engage the internal surface or portion 308 of the base tube 292 to at least assist in fixing or holding the guide tube 234 relative to the skull 20h. As discussed above, the adjustable member 292 may be fixed relative to the base portion 280 and the base portion 280 may be fixed relative to the skull 20h. Therefore, the alignment tube 234 may be held in a selected position with the adjustable or robotic portions 220, 224 and/or the lockable base 280 relative to the skull 20h.

In various embodiments, the internal surface 308 of the adjustable tube 292 may include a dimension 312 that may be an internal dimension of the adjustment tube 292. The guide tube 234 may include an external dimension 316 that is smaller than the internal dimension 312. Thus, the alignment tube 234 may be adjusted relative to the adjustment base 280.

In various embodiments, the alignment tube 234 may be moved to a selected position that may be pre-planned or pre-determined. The tracking device 270 may be used to track the position of the alignment tube or device 234 to the pre-determined position. The adjustable base 280 may be moved to a position and engage the guide tube 234 in a selected manner, such as with a friction or contact fit. Therefore, the alignment guide 234 may be held relative to the adjustable base 280. The adjustable base 280 may then be fixed relative to the skull 20h, such as with the fixation members 288 and/or selected adjustable locking features. In various embodiments, the adjustable tube portion 292 may be locked relative to the base portion 284 with appropriate locking features or portions 293, such as thumb screws or the like, similar to those included in the Nexframe® trajectory guide sold by Medtronic, Inc., having a place of business in Minnesota. The adjustable member 292 may, therefore, be engaged in a selected manner to the guide tube 234 and then fixed in the appropriate or selected position relative to the base 284, which, in turn, is fixed to the skull 20*h*. Accordingly, the adjustable base 280 may assist in fixing the guide tube 234 relative to the skull 20*h*, for a selected period, such as during a procedure.

With continuing reference to FIGS. 2 and 3, and additional reference to FIG. 4 and FIGS. 5A-5C, the alignment system 200, which may include the guide tube 234 and the base 280 may be used to assist or guide a procedure on the subject 20. The procedure or process may be included or described in the flow chart 360 illustrated in FIG. 4. The process may begin in block 364, which may include various features or processes, such as diagnosing the subject, identifying a possible diagnosis, determining a possible treatment plan, or other appropriate procedures. Accordingly, the procedure may start in block 364. Following the starting of the procedure in block 364, the procedure 360 may include a plurality of paths including a first path to acquire and/or access image data in block 368. The image data may be acquired of the subject 20 to assist in performing a procedure on the subject 20 and/or diagnosing the subject, planning a procedure for the subject, or the like. The image data may include image data of a selected portion of the subject, such as of the head 20 *h*. The image data may include image data acquired with the imaging system 24, or any appropriate imaging system, such as a magnetic resonance imaging system (MRI), or the like. In various embodiments, the image data may be used to generate images that may be displayed on the display device 32. The image data may be acquired of the subject 20 at any appropriate time, such as prior to positioning the alignment system 200 relative to the subject. For example, a procedure may be planned relative to the subject 20, including a pose or position/location of the guide in block 372. For example, an entry point and trajectory may be determined to perform a procedure, such as for a tumor resection, DBS placement, or the like. Accordingly, a procedure may be planned, such as with using image data acquired and/or accessed of the subject 20.

A plan may be recalled in block 378 of a guide pose, in addition to or alternatively to performing the planning procedure in block 368. Accordingly, the procedure 360 need not include planning a procedure. Rather a procedure may be planned in any appropriate time and the user 12 may recall the plan for the procedure when the subject 20 is prepared for the procedure, such as in an operating room with the navigation system 10. Accordingly, the plan may be developed and saved for a later use which may then be recalled. The plan may be saved in an appropriate memory, such as the navigation memory 74 and may be recalled with the processor module 70.

The guide system 200 may be positioned relative to the subject in block 382. The guide system 200 may be used to move the guide tube 234 to the planned pose for the guide. The guide may be positioned, such as in an initial position relative to the subject 20 and moved further thereafter. With reference to FIG. 5A, for example, the alignment system 200 may be fixed with the stand 204, which may be fixed to the patient support 26, relative to the subject head 20*h*. The second portion 224 may move relative to the first portion 220 to move the guide 234 relative to the subject head 20*h*. The tracking device 270 may be used to track the guide tube 234. The tracking system may track the position of the guide member 234 such as with the tracking device 270. The position of the guide tube 234 may be illustrated on the display device with the icon 234' due to registration of the subject space, such as the subject head 20*h* to the image 30 in block 386, as discussed above.

Therefore, the guide tube 234 may be navigated relative to the subject head 20*h*. The pose of the guide tube may be illustrated with the graphical representation 234' relative to the image 30 on the display device 32. Due to navigation of the guide tube 234, the planned position may be determined or identified such as with an output on the display 32 at a selected time. Therefore, the guide tube may be moved and navigated to the planned pose in block 390.

Once the guide tube 234 is at the predetermined or planned position, an indication or alert 396 may be given to the user 12, such as with an alert on the display device 32, an audible alert, or other appropriate alert. Accordingly, the user 12 may move or operate the alignment system 200 to move the guide tube 234 to the planned position. It is further understood that the alignment system may be substantially automatic and operated by the processor module 70 to move the guide tube 234 due to the plan. As the plan may be recalled and/or determined and the navigation system may navigate the guide tube 234, the alignment system 200 may move due to automatic movement of the robotic system to move the guide tube 234 substantially automatically to the planned position. Accordingly, the guide tube 234 may be manually moved, such as operation of the alignment system 200 by the user 12, and/or automatically by operating the alignment system 200 with the appropriate system, such as the navigation system 10.

Once the alignment tube 234 is at the pre-planned position, a marking device 396 may be used to mark a position 400 on the subject head 20*h* in block 404. Marking the position on the subject head 20*h* may be optional, but may be useful for positioning the adjustable base 280 relative to the subject head 20*h*.

Accordingly, with continuing reference to FIG. 4 and reference to FIG. 5B, the adjustable base 280 may be positioned relative to the subject head 20*h* in block 410. The adjustable base 280 may be moved to the head 20*h* and fixed relative thereto with the appropriate fixation devices 288. As discussed above, the base 280 may be positioned on the head 20*h* at the position of the mark 400, or due to the identified gross position of the alignment tube 234.

During positioning of the base 280, the alignment system 200 may be moved relative to the subject 20. As discussed above, the support portion 204 may be movable or adjustable and, therefore, the movable members 220, 224 may be moved to a second location to allow for efficient and fast application and fixation of the adjustable base 280 relative to the subject 20. If the alignment system 200 is moved relative to the subject, therefore, re-alignment of the guide to the planned pose in block 420 may occur.

Accordingly, whether the guide is re-aligned in block 420, where the base 280 is fixed to the subject 20*h* with the guide tube 234 in place, the guide tube 234 may engage the base guide tube 292. When the guide tube 234 is at the planned position and engages the base guide tube 292 the alignment through the guide tube 234 and the base guide 292 is understood to be along the planned pose or trajectory. Thus, engaging the guide tube 234 into the base guide tube 292 in block 424 may align the guide tube 234 relative to the subject 20*h*. Further engaging the base system 280 in a substantially fixed position, such as fixing the base 284 to the head and fixing the base tube 292 relative to the base 284, provides a mechanical fixation of the guide tube 234 relative to the subject head 20*h*. Therefore, the guide tube 234 may be secondarily and/or mechanically fixed relative to the subject 20*h* for a selected procedure.

Further, the display device 32 may display an indication, such as the indication 396, that the alignment is at the appropriate position. The display device 32 may thus display an icon of the guide tube 234'.

Once the alignment is in the appropriate or pre-planned position, the instrument 16 may be positioned relative to the guide tube 234 to assist in performing the procedure. The instrument 16 may be and move and/or track relative to the subject 20h in block 430. The display device 32 may display the graphical representation 16' of the instrument during navigation and use of the instrument, even within the guide tube 234. It is understood, however, that illustration of the instrument icon 16' when in the guide tube 234 is not required.

The instrument 16 may then be used to perform the procedure in block 434. Performing the procedure may include positioning an appropriate portion through the guide 234, such as a DBS lead, or resection instrument, or the like. It is understood that any appropriate procedure may be performed with the instrument 16 and the instrument 16 may be any appropriate instrument. The method 360 may then end in block 438. Ending the procedure in block 438 may include any appropriate steps such as completing navigation, performing a resection, performing an implantation, or the like.

The procedure 360, therefore, may use the alignment system 200 to assist in performing a procedure relative to the subject 20. In various portions of the procedure 360, the navigation system or any appropriate processor module may be used to navigate the guide tube 234, determine and identify that the guide tube is at a planned pose, automatically move the guide tube 234, or other appropriate portions. It is also understood that the user 12 may be used or operate portions of the alignment system 200 and/or move instruments relative to the guide tube 234.

It is understood by one skilled in the art, the procedure 360 does not require all portions identified therein. Generally, the procedure may include moving the guide to the planned pose in block 390 and engaging the guide to the base in block 424. The guide tube 234 may be moved in an appropriate manner to the planned pose and may be tracked, as discussed above. The base system 280 may then be used to assist in holding (e.g. mechanically fix) the guide tube 234 relative to the subject.

Further, while the procedure is illustrated relative to the head 20h of the subject 20, it is understood that the alignment system 200 may be used for other appropriate procedures. In various embodiments, the guide system 200 may be used to guide or align the guide tube 234 relative to a spinal procedure, a biopsy procedure in any appropriate organ (e.g. heart, lung, liver, etc.). Further, the procedure 360 and the alignment system 200 may be used for appropriate procedures on non-living or inanimate objects, such as moving an instrument or driving movement of an instrument into an inanimate object. Therefore, the alignment system 200 may be used to perform a procedure on any appropriate subject.

Turning reference to FIG. 6A and FIG. 6B, the alignment system 200, as discussed above, may be provided with an adjustable base 500 in an alignment system 200'. The alignment system 200' may be substantially similar or include identical portions or similar portions to those discussed above, and/or alternative or different portions, as discussed further herein. Similar portions will be identified with similar reference numerals augmented by a prime (').

With initial reference to FIG. 6A, the subject may have the alignment system 200' positioned relative to the head 20h. The alignment system 200' may include a first portion 224' that may move relative to a base or second portion 220'.

Again, as discussed above, a support 204' may be fixed relative to the patient support 26 and assist in holding the alignment system 200' in a relative position to the subject head 20h. The alignment system 200' may include a guide member 504. The guide member may be a guide tube with a bore. The guide tube 504 may include the tracking device or tracking device 270'. The tracking device 270' may be used to track a pose of the guide tube 504 relative to the subject 20h and may be displayed on the display device 32, similar to the guide tube 234 as discussed above.

The adjustable base 500 may include a base portion 510 that may be fixed to the subject head 20h with the fixation devices 288', as discussed above. The adjustable base 500 may further include an adjustable portion 514 that may move relative to the base 510 and/or be fixed relative to the base 510, as discussed above. Accordingly, the adjustable portion 514 may move relative to the base 510 for achieving a selected alignment of the guide tube 504 relative to the subject 20h.

The adjustable base 500, however, may be movably fixed relative to the guide tube 504. For example, the guide tube 504 may include an external thread and the adjustable portion 514 may include an internal thread. By rotating the base tube 514 and/or the guide tube 504, the adjustable base 500 may move axially along an axis 520 relative to the guide tube 504 generally in the direction of the double headed arrow 524. In various embodiments, the axis 520 may be a longitudinal axis of the guide tube 504.

During a gross or initial alignment of the guide tube 504 relative to the head 20h, the adjustable base 500 may be in a first position, as illustrated in FIG. 6A, that is not in contact with the head 20h. Once the alignment is determined to be in an appropriate position, such as with an output 530 on the display device 32, the adjustable base 500 may be moved relative to the head 20h. Therefore, the initial alignment or alignment of the guide tube 504 may be made with the adjustable base 500 attached thereto, but not in contact with the head 20h.

With reference to FIG. 6B, once the guide tube 504 is in the appropriate or pre-planned position, the adjustable base may be moved toward the head 20h, such as in the direction of arrow 524a. Movement of the base 500 relative to or toward the head 20h may be due to rotation of the base tube 514 and/or rotation of the guide tube 504. Accordingly, the adjustable base 500 may then be move relative to, such as within contact, with the head 20h and fixed relative thereto, such as with the patient fixation portions 288.

It is understood that the adjustable base 500 may be moved relative to the guide tube 504 with any appropriate mechanism, such as with the turning mechanism, as discussed above, a ratchet and pawl, a detent, or other appropriate mechanism. It is further understood that appropriate connection or movement mechanisms may include a set screw that may be engaged and disengaged from between the two guide tubes 504, 514 to allow for movement of the adjustable base 500 relative to the head 20h.

Accordingly, as discussed above, the guide tube, according to various embodiments 234, 504, may be moved to a planned or selected pose relative to the subject 20. The adjustable base, according to various embodiments 280, 500 may then be fixed relative to the head 20h and engage the guide tube 234, 504 to provide for a mechanical and/or secondary fixation relative to the subject 20. The respective guide tubes 234, 504 may be used to assist in guiding the instrument 16 relative to the subject 20 for performing a procedure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, graphic processing units (GPUs), application specific integrated circuits (ASICs), field programmable logic arrays (FPGAS), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system to position a guide member relative to a subject for a selected procedure, comprising:
a movement system to move the guide member relative to the subject while being navigated, wherein the movement system is configured to fix the guide member relative to the subject when the guide member is in a selected guide pose; and
a base system to (i) cooperate with the guide member and (ii) be fixed to the subject to at least assist in holding the guide member relative to the subject;
wherein the base system has (i) a cooperating member configured to cooperate with the guide member to assist in fixing the guide member in the selected guide pose and (ii) a fixation member configured to be fixed to the subject;
wherein the cooperating member is movable relative to the fixation member;
wherein the base system is axially movable between a first position and a second position relative to the guide member when the guide member is fixed in the selected guide pose, and wherein the base system is moved relative to the subject and axially relative to the guide member between the first position and the second position.

2. The system of claim 1, wherein the movement system further comprises:
a robotic system configured to be positioned near the subject, the robotic system having at least one member to engage and move the guide member;
wherein the robotic system is further configured to be operated to move the guide member relative to the subject.

3. The system of claim 1, further comprising: a tracking system to track the guide member relative to the subject.

4. The system of claim 3, further comprising:
a display to display a position of the guide member relative an image defining an image space.

5. The system of claim 1, wherein the cooperating member is selectively fixable in one of a plurality of positions relative to the fixation member.

6. The system of claim 5, wherein the cooperating member is releasably fixed relative to the fixation member.

7. The system of claim 6, wherein the fixation member is releasably fixed relative to the subject.

8. The system of claim 7, further comprising:
an instrument used with the guide member through at least a portion of the base system to the subject.

9. The system of claim 1, wherein the movement system moves the guide member and the base system to a first pose with the base system in the first position and the guide member in the selected guide pose; and
wherein the base system is moved to the second position after the guide member is in the selected guide pose.

10. The system of claim 9, wherein the base system is moved to the second position by rotating at least a portion of the base system relative to the guide member to move the base system axially relative to the guide member.

11. The system of claim 1, wherein the base system is not in contact with the subject when the base system is in the first position, and wherein the base system contacts the subject in the second position.

12. The system of claim 1, wherein moving the base system to the second position includes rotating at least a portion of the base system relative to the guide member to move the base system relative to the subject and axially relative to the guide member.

13. A method of positioning a guide member, comprising:
operating a movement system to move the guide member;
registering an image;
navigating movement of the guide member to a selected pose;

fixing the guide member relative to a support structure in the selected pose;

fixing a base system, wherein the base system includes a cooperating portion movable relative to a base portion;

moving the cooperating portion relative to the base portion;

engaging the guide member with the cooperating portion by positioning the guide member within the cooperating portion;

fixing the cooperating portion relative to the base portion; and axially moving the base system relative to the guide member from a first position to a second position when the guide member is fixed relative to the support structure in the selected pose;

wherein engaging the guide member with the cooperating portion and fixing the cooperating portion relative to the base portion assists in holding the guide member at the selected pose.

14. The method of claim 13, wherein engaging the guide member with the cooperating portion and axially moving the base system relative to the guide member occurs after the guide member is navigated to the selected pose.

15. The method of claim 13, further comprising: predetermining the selected pose.

16. A system to position a guide member for a selected procedure, comprising:

a movement system to move the guide member relative to a subject;

a support to fix the movement system and the guide member relative to the subject;

a base system configured to be selectively fixed relative to the subject, wherein the base system includes a cooperating portion movably attached to a base portion; and a fixation system configured to selectively fix the cooperating portion relative to the base portion;

wherein the cooperating portion is configured to receive the guide member to couple the base system to the guide member;

wherein the cooperating portion is movable relative to the base portion;

wherein the base portion is configured to be selectively fixed to the subject;

wherein the base system is axially movable relative to the guide member when the guide member is fixed relative to the subject such that the base system moves relative to the subject.

17. The system of claim 16, further comprising:

a navigation system comprising a tracking system to track a pose of the guide member.

18. The system of claim 16, wherein the cooperating portion includes a bore configured to axially receive the guide member to assist in holding the guide member at a selected pose.

19. The system of claim 16, wherein the fixation system includes at least a fixation member configured to be positioned in an unengaged position and in an engaged position, wherein the engaged position selectively fixes the cooperating portion relative to the base portion;

wherein the cooperating portion is configured move relative to the base portion when the fixation member is in unengaged position.

20. The system of claim 16, further comprising:

an axial positioning portion configured to selectively position the base system between a first axial position and a second axial position relative to the guide member upon the cooperating portion axially receiving the guide member.

* * * * *